(12) United States Patent
Mallin

(10) Patent No.: US 9,889,274 B2
(45) Date of Patent: Feb. 13, 2018

(54) SKIVE-LESS SHEATH

(71) Applicant: Medtronic CryoCath LP, Toronto (CA)

(72) Inventor: George D. Mallin, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 258 days.

(21) Appl. No.: 14/743,317

(22) Filed: Jun. 18, 2015

(65) Prior Publication Data

US 2016/0367786 A1   Dec. 22, 2016

(51) Int. Cl.
*A61M 25/01*   (2006.01)
*A61M 39/06*   (2006.01)

(52) U.S. Cl.
CPC ........ *A61M 25/0147* (2013.01); *A61M 39/06* (2013.01); *A61M 2039/062* (2013.01)

(58) Field of Classification Search
CPC ............. A61M 25/0147; A61M 39/06; A61M 2039/062; A61M 29/00; A61B 17/34; A61B 17/3405; A61B 17/3415; A61B 17/3417; A61B 1/34; A61B 1/3405; A61B 1/3415; A61B 1/34177
See application file for complete search history.

(56) References Cited

U.S. PATENT DOCUMENTS

| | | | |
|---|---|---|---|
| 4,134,402 A | 1/1979 | Mahurkar | |
| 4,610,665 A * | 9/1986 | Matsumoto | ....... A61M 39/0606 604/167.04 |
| 4,643,711 A | 2/1987 | Bates | |
| 5,061,273 A | 10/1991 | Yock | |
| 5,207,649 A * | 5/1993 | Aruny | ............... A61M 39/0606 251/149.1 |
| 5,250,038 A | 10/1993 | Melker et al. | |
| 5,328,480 A | 7/1994 | Melker et al. | |
| 5,599,299 A | 2/1997 | Weaver et al. | |
| 6,146,354 A | 11/2000 | Beil | |
| 6,228,052 B1 | 5/2001 | Pohndorf | |
| 6,280,433 B1 | 8/2001 | McIvor et al. | |
| 6,379,346 B1 | 4/2002 | McIvor et al. | |
| 6,533,782 B2 | 3/2003 | Howell et al. | |
| 6,827,710 B1 | 12/2004 | Mooney et al. | |
| 6,945,956 B2 | 9/2005 | Waldhauser et al. | |
| 7,066,925 B2 | 6/2006 | Gately et al. | |
| 7,871,398 B2 | 1/2011 | Chesnin et al. | |
| 7,896,853 B2 | 3/2011 | Triplett et al. | |
| 7,974,710 B2 | 7/2011 | Seifert | |

(Continued)

*Primary Examiner* — Kevin C Sirmons
*Assistant Examiner* — Amber Stiles
(74) *Attorney, Agent, or Firm* — Christopher & Weisberg, P.A.

(57) ABSTRACT

An introducer sheath that is coupled to or integrated with a secondary device insertion hub, such as a hemostasis valve hub, wherein the secondary device insertion hub is received within a proximal portion of the introducer sheath. The introducer sheath may include one or more pull wire lumens, and the secondary device insertion hub does not cover or obstruct the proximal opening of each of the one or more pull wire lumens when coupled to or integrated with the introducer sheath. In this configuration one or more pull wires are free to exit the one or more pull wire lumens through a proximal face of the introducer sheath instead of a skive in a wall of the elongate body.

18 Claims, 7 Drawing Sheets

(56) References Cited

U.S. PATENT DOCUMENTS

| | | |
|---|---|---|
| 8,162,878 B2 | 4/2012 | Bonnette et al. |
| 8,303,568 B2 | 11/2012 | Gately et al. |
| 8,357,127 B2 | 1/2013 | Triplett et al. |
| 2002/0072712 A1 | 6/2002 | Nool et al. |
| 2004/0176739 A1 | 9/2004 | Stephens et al. |
| 2005/0059958 A1 | 3/2005 | Lessard et al. |
| 2005/0197624 A1 | 9/2005 | Goodson, IV et al. |
| 2006/0135962 A1 | 6/2006 | Kick et al. |
| 2010/0130936 A1* | 5/2010 | Voss .................. A61M 25/0009 604/158 |
| 2013/0123622 A1* | 5/2013 | Tchirikov .............. A61M 25/02 600/435 |
| 2014/0364939 A1 | 12/2014 | Deshmukh et al. |

\* cited by examiner

SKIVE-LESS SHEATH

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to skiveless sheath. In particular, the present invention relates to an introducer sheath that is coupled to or integrated with a secondary device insertion hub, such as a hemostasis valve hub, wherein the secondary device insertion hub is received within a proximal portion of the introducer sheath and does not obstruct one or more pull wire lumens within the introducer sheath.

BACKGROUND OF THE INVENTION

Intracardiac and intravascular procedures, commonly involve the use of an introducer sheath. The introducer sheath facilitates insertion of one or more medical devices, such as ablation catheters, mapping catheters, transseptal puncture devices, and the like, and their navigation through the patient's vasculature. An introducer sheath typically includes a hemostasis valve, which may be used to prevent the backflow of blood out of the introducer sheath during insertion of the medical devices into the sheath.

An introducer sheath may be attached to a hemostasis valve by inserting a proximal end of the sheath into a hemostasis valve hub and bonding the sheath and hub together. Thus, the hemostasis valve hub encloses the proximal end of the introducer sheath and therefore closes off any lumens within the sheath. In the case of steerable introducer sheaths, the sheath wall may include a skive hole that provides an exit from the sheath for each pull wire. As shown in FIG. 1, a currently known introducer sheath 10 may include a proximal portion 12 that is coupled to a hemostasis valve hub 14. Further, the proximal portion of the pull wire 16 may exit the sheath through a skive hole 18 and, once outside the sheath 10, may be connected to one or more steering elements and/or directly manipulated by an operator to navigate the sheath (not shown).

However, sheaths having skive holes 18 frequently develop leaks, and this may be due to the manner in which the pull wire 16 exits the sheath 10 and/or the mechanical means by which the skive holes 18 are created.

It is therefore desirable to provide a steerable introducer sheath having a hemostasis valve hub that eliminates the need for skive holes.

SUMMARY OF THE INVENTION

The present invention advantageously provides an introducer sheath that is coupled to or integrated with a secondary device insertion hub, such as a hemostasis valve hub, wherein the secondary device insertion hub is received within a proximal portion of the introducer sheath and does not obstruct one or more pull wire lumens within the introducer sheath. An introducer sheath may include an elongate body having a proximal portion, a distal portion, and a lumen therebetween and a secondary device insertion hub. The secondary device insertion hub may be received within the proximal portion of the elongate body, the lumen being unobstructed by the secondary device insertion hub. The lumen may be a pull wire lumen, the introducer device further comprising a main lumen that is substantially parallel to the pull wire lumen. Further, the main lumen may have a first inner diameter at the distal portion of the elongate body and a second inner diameter at the proximal portion of the elongate body, and the first inner diameter and the second inner diameter may be different. For example, the inner diameter at the proximal portion of the elongate body may be greater than the inner diameter at the distal portion of the elongate body. The pull wire lumen may be a distance from the main lumen, the distance being the same in the proximal portion of the elongate body as in the distal portion of the elongate body. The proximal portion of the elongate body may define a proximal face, and the device may further include a pull wire within the pull wire lumen, with at least a portion of the pull wire exiting the proximal portion of the elongate body through the proximal face. For example, the proximal face may define a proximal opening of the pull wire lumen and a proximal opening of the main lumen. The elongate body may define a longitudinal axis, and the proximal portion of the pull wire lumen may be at an angle of between approximately 10° and approximately 45° from the longitudinal axis, whereas the main lumen may lie entirely along the longitudinal axis. The secondary device insertion hub may be integrated with the proximal portion of the elongate body. Further, the secondary device insertion hub may be hemostasis valve hub.

An introducer sheath may include an elongate body having a proximal portion, a distal portion, and a longitudinal axis; a main lumen defined by the elongate body and extending between the proximal portion of the elongate body and the distal portion of the elongate body, the main lumen having a proximal opening; a pull wire lumen defined by the elongate body and extending between the proximal portion of the elongate body and the distal portion of the elongate body, the pull wire lumen having a proximal opening; and a secondary device insertion hub, the secondary device insertion hub being received within the proximal opening of the main lumen, the proximal opening of the pull wire lumen being unobstructed by the secondary device insertion hub. The main lumen may have a distal portion having a first inner diameter and a tapered portion between the distal portion and the proximal opening of the main lumen. The proximal opening of the main lumen may have a second inner diameter and the tapered portion may have a continuously decreasing inner diameter from the proximal opening to the distal portion of the main lumen. The proximal portion of the elongate body may define a proximal face, which may include the proximal opening of the pull wire lumen and the proximal opening of the main lumen.

A medical device may include an elongate body having a proximal portion, a distal portion, and a longitudinal axis; a main lumen defined by the elongate body and extending between the proximal portion of the elongate body and the distal portion of the elongate body along the longitudinal axis of the elongate body, the main lumen having a distal portion, a proximal opening, and a tapered portion between the proximal opening and the distal portion of the main lumen; a pull wire lumen defined by the elongate body and extending between the proximal portion of the elongate body and the distal portion of the elongate body, the pull wire lumen having a distal portion, a proximal portion, and a proximal opening; and a secondary device insertion hub at least partially disposed within the proximal opening and tapered portion of the main lumen, the proximal opening of the pull wire lumen being unobstructed by the secondary device insertion hub, the distal portion of the pull wire lumen being at least substantially parallel to the longitudinal axis and the proximal portion of the pull wire lumen being at an angle from the longitudinal axis that follows an angle of the tapered portion of the main lumen. The proximal portion of the pull wire lumen may be at an angle of between approximately 10° and approximately 45° from the longitudinal axis of the elongate body.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 2:
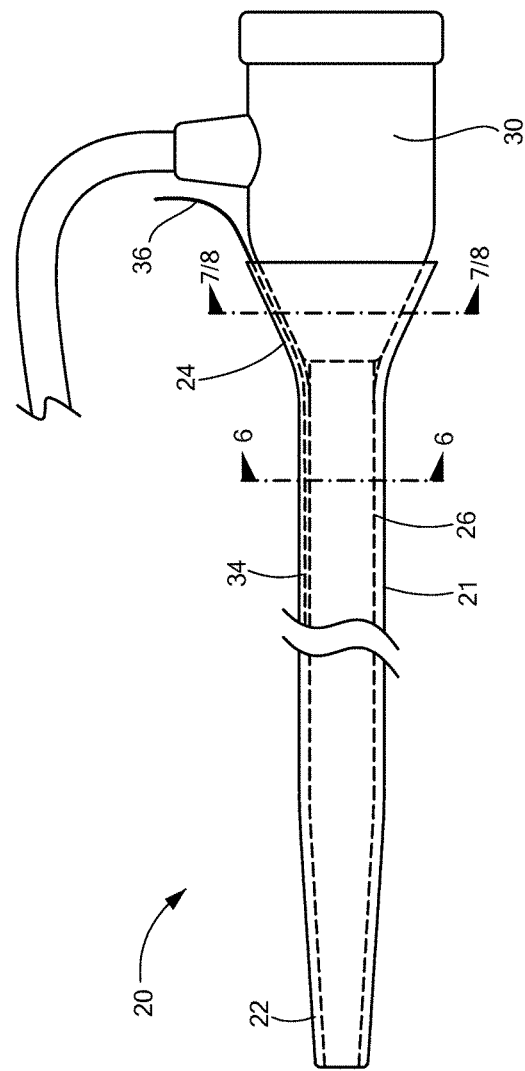
FIG. 2 shows a skiveless introducer sheath with a hemostasis valve assembly.
Figure 3:
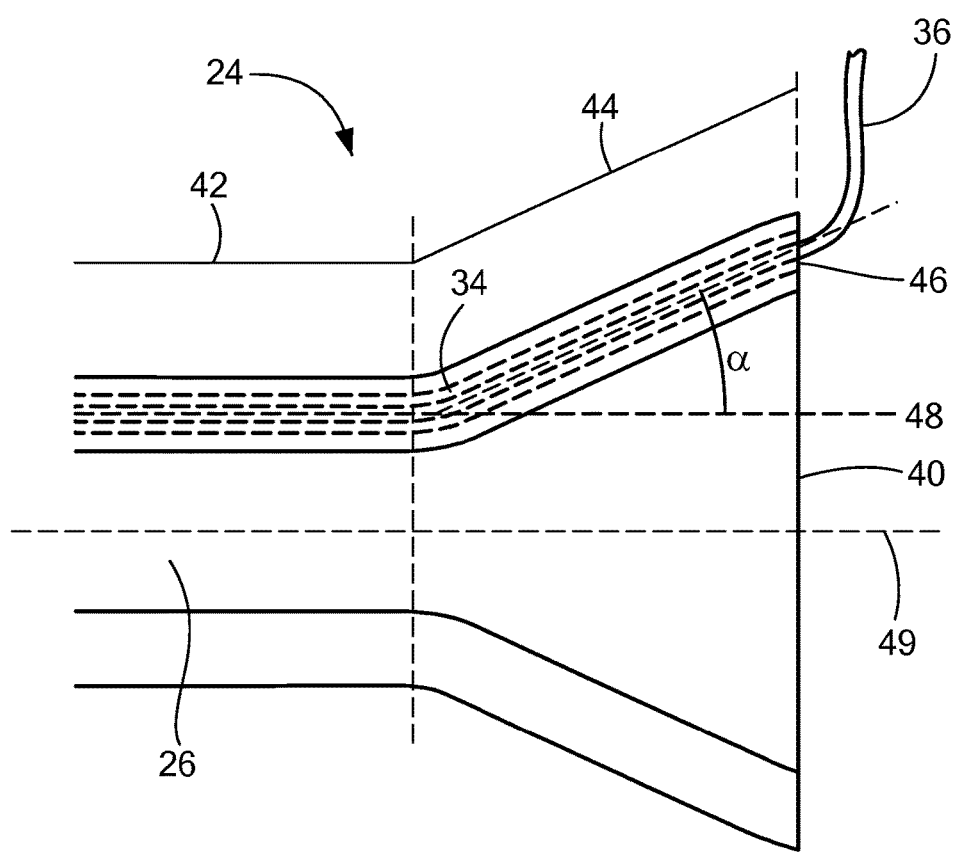
FIG. 3 shows a close-up, cross-sectional view of a proximal portion of a skiveless introducer sheath.

Referring now to the figures in which like elements are numbered alike, FIG. 2 shows a skiveless introducer sheath with a hemostasis valve assembly. The sheath 20 may generally include an elongate body 21 including a distal portion 22, a proximal portion 24, and a main lumen 26 therebetween. The distal portion 22 of the sheath 20 may be configured for insertion into a patient's vasculature. The proximal portion 24 of the sheath 10 may be coupled to a hub 30 through with a secondary device may be introduced into the patient's vasculature through the sheath 20. Accordingly, the hub 30 may be referred to as a "secondary device insertion hub." For example, the proximal portion 24 may be coupled to a hemostasis valve hub. The sheath 20 may further include one or more pull wire lumens 34 and one or more pull wires 36.

Figure 1:
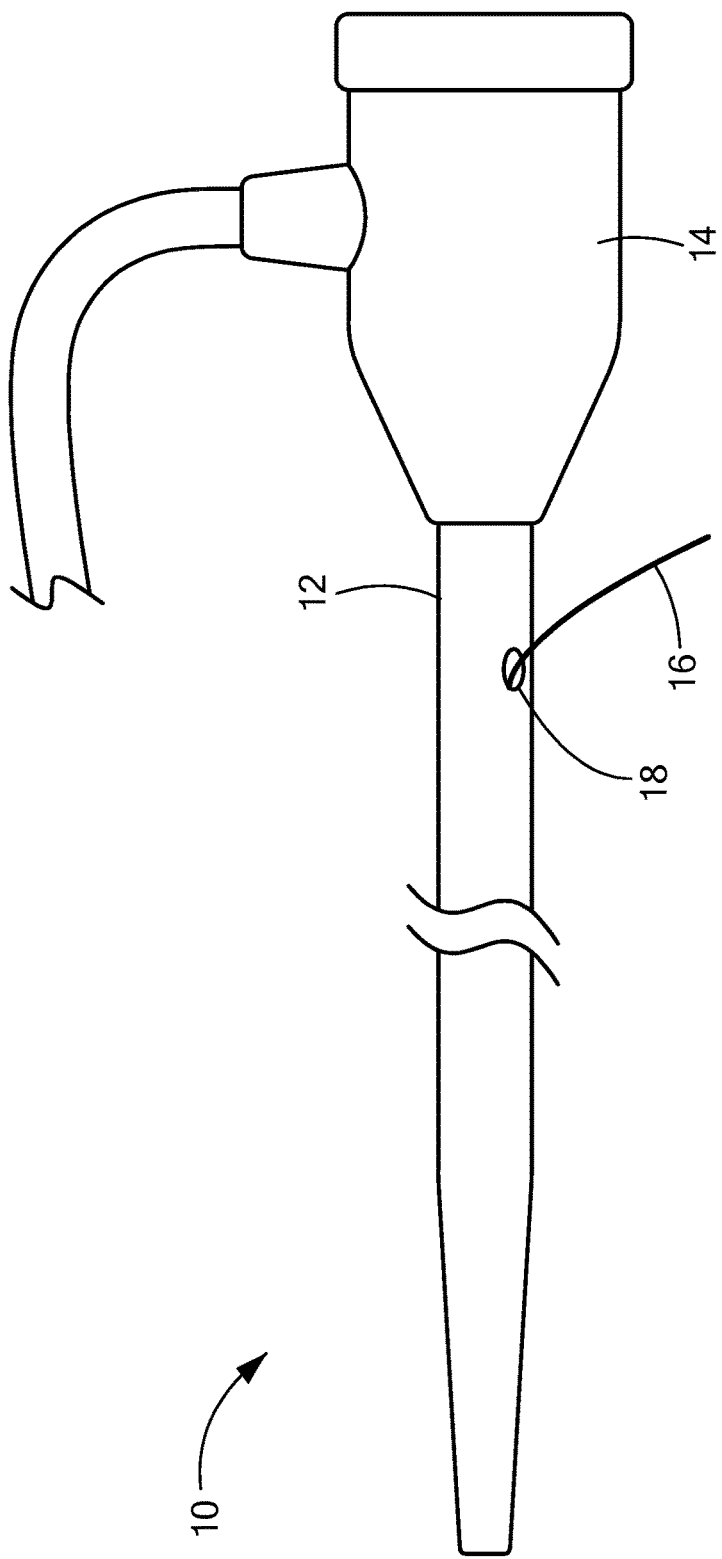
FIG. 1 shows an introducer sheath as known in the prior art, the sheath having skive holes.
Figure 4:
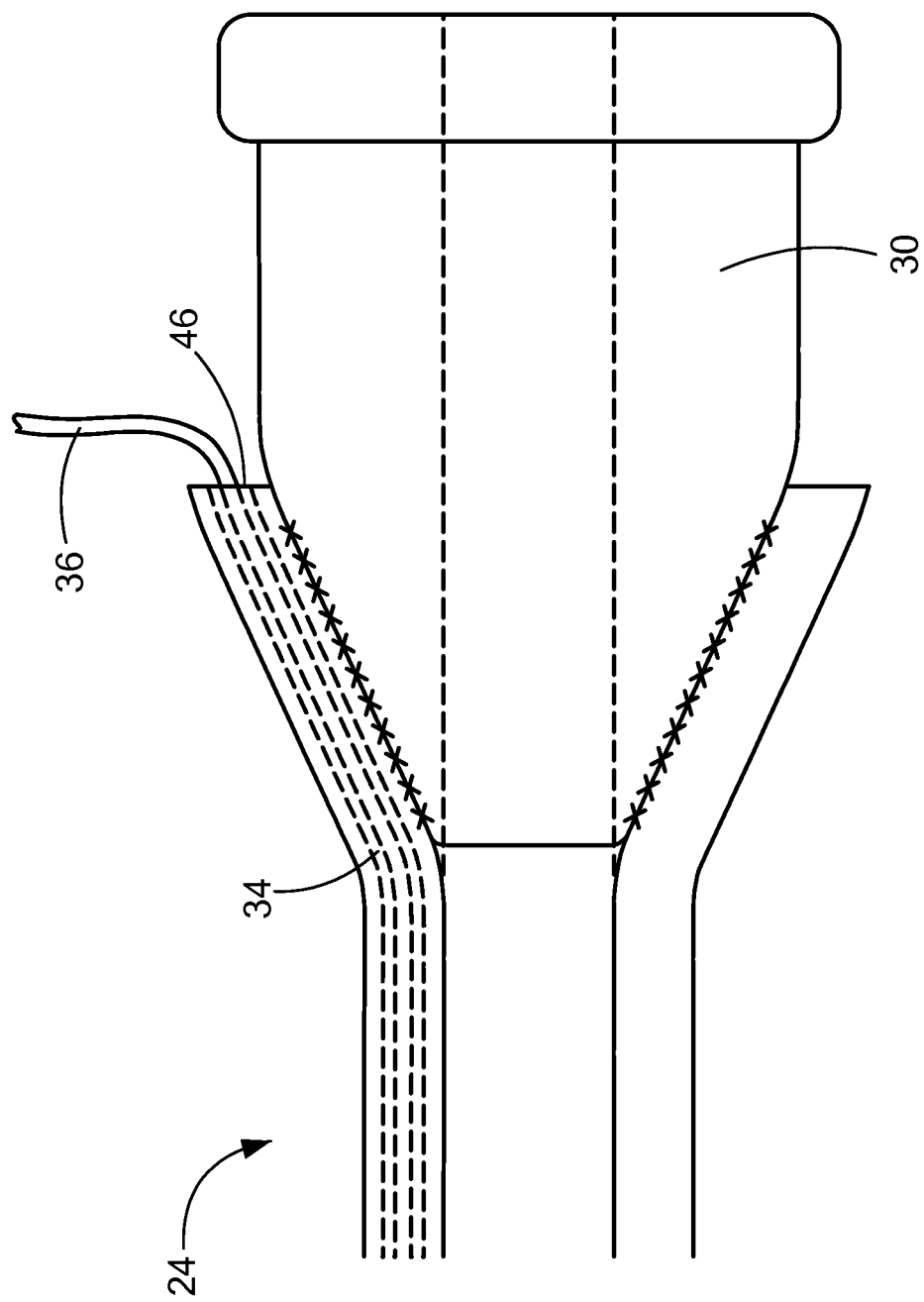
FIG. 4 shows a close-up, cross-sectional view of a proximal portion of a skiveless introducer sheath coupled to a hub.
Figure 5:
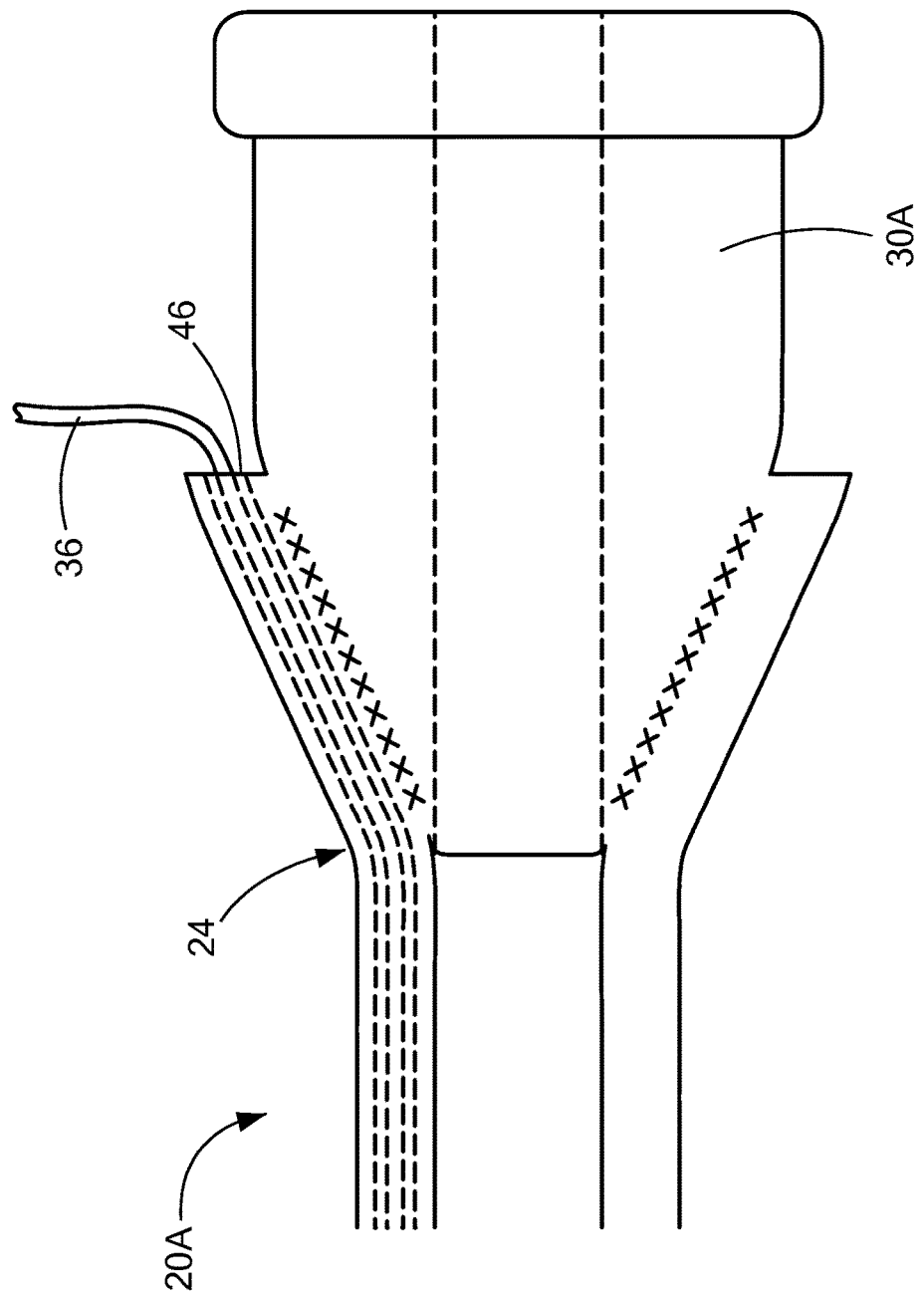
FIG. 5 shows a close-up, cross-sectional view of a proximal portion of a skiveless introducer sheath with an integrated hub.
Figure 6:
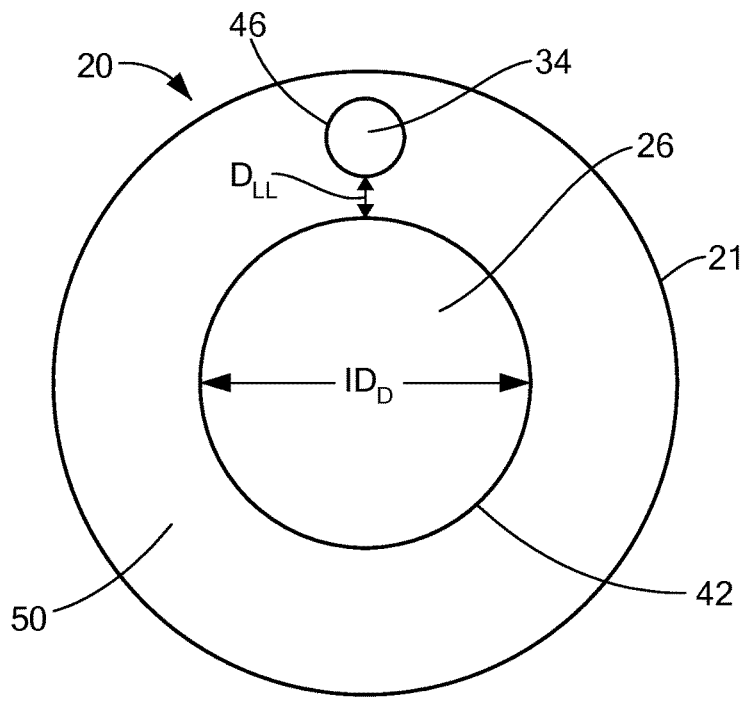
FIG. 6 shows a cross-sectional view of a distal portion of the skiveless sheath.
Figure 7:
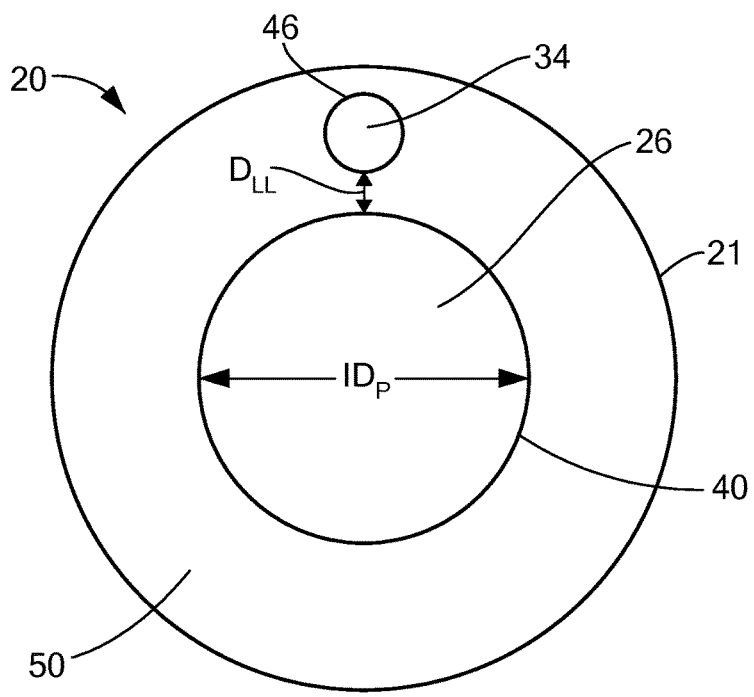
FIG. 7 shows a cross-sectional view of a proximal portion of the skiveless sheath.

Referring now to FIGS. 3-8, the proximal portion of the skiveless sheath is shown in more detail. Unlike the proximal portion 12 of the prior art sheath 10 shown in FIG. 1, the sheath 20 may include a proximal portion 24 that is widened. That is, the proximal portion 24 may be tapered from the main lumen proximal opening 40 in a proximal-to-distal direction. As is shown in FIGS. 6 and 7, the main lumen 26 may include a distal portion 42 with a continuous inner diameter $ID_D$ that is smaller than the inner diameter $ID_P$ of the proximal opening 40 of the main lumen 26. The main lumen 26 may further include a tapered portion 44 between the distal portion 42 and the proximal opening 40 that has a continually decreasing inner diameter from the proximal opening 40 to the distal portion 42 of the main lumen 26. The sheath may also have a shape, including a tapered portion that follows the shape of the main lumen 26. The proximal opening 40 of the main lumen 26 may be sized to receive a hub 30 therein, such as a hemostasis valve hub. As shown in FIG. 6 (cross-sectional view of the distal 22 portion of the sheath 20 along line 6-6 in FIG. 2) and FIG. 7 (cross-sectional view of the proximal portion 24 of the sheath 20 along line 7/8-7/8 in FIG. 2, shown without the hub 30), the inner diameter $ID_D$ of the distal portion 22 may be smaller than the inner diameter $ID_P$ of the proximal portion 24. The main lumen 26 may be located in the center of the sheath 20 (that is, may lie along the central axis) or may be offset from the central axis of the sheath 20.

As is shown in FIG. 4, the hub 30 may be received within a proximal opening 40 of the main lumen 26. The hub 30 and the sheath 20 may be composed of the same material or different materials. The hub 30 and the sheath 20 may be affixed to each other by, for example, adhesives, friction fitting, chemical bonding, and/or other means known in the art. Alternatively, as shown in FIG. 5, the hub 30A and the sheath 20 may be composed of the same material and may be coupled in a way that integrates the hub 30A with the sheath 20 to create a single-piece hub/sheath device 20A, such as along the hash marks shown in FIG. 5. As a non-limiting example, the hub/sheath device 20A may be formed by Pebax reflow, or a soft thermoplastic valve may be fit into the shaft, with the sheath itself acting as the valve hub.

Figure 8:
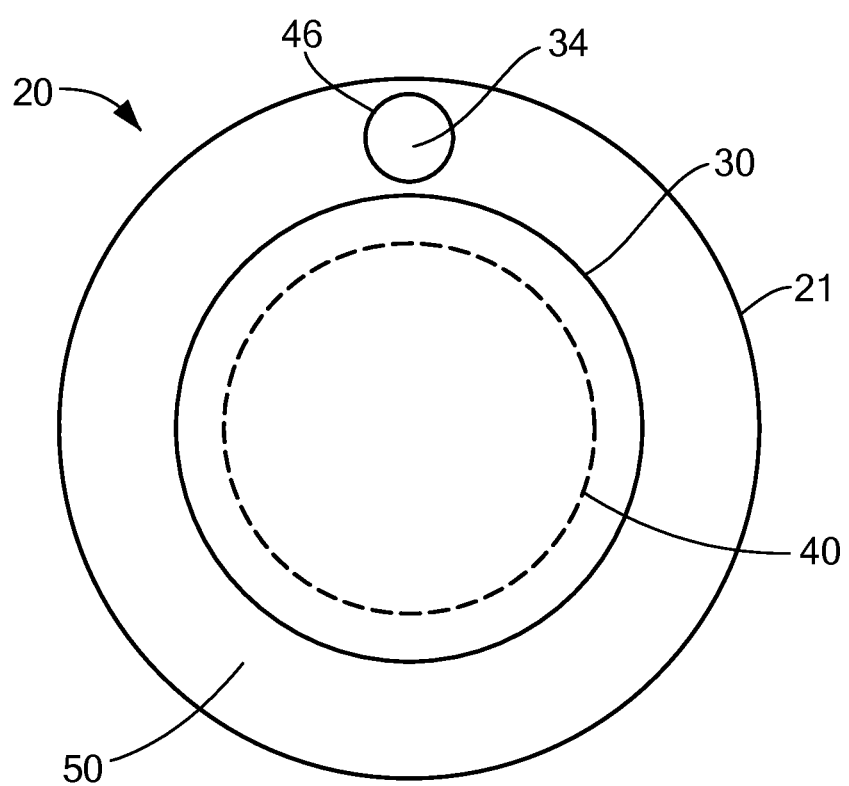
FIG. 8 shows a cross-sectional view of the proximal portion of the skiveless sheath, the sheath coupled to a hub.

The one or more pull wire lumens 34 may be at least substantially parallel to the main lumen 26 and the proximal opening 46 may be located on the outside of the main lumen proximal opening 40. If the sheath 20 includes more than one pull wire lumen 34, the proximal openings 46 of the pull wire lumens 34 may be radially distributed about the main lumen proximal opening 40, either symmetrically or non-symmetrically. Although one pull wire lumen 34 is shown in FIGS. 6-8, it will be understood that the sheath 20 may include more than one pull wire lumen 34. Further, the proximal portion of each of the one or more pull wire lumens 34 may be angled (the angle is represented by a in FIG. 3) from the main longitudinal axis 48 of the pull wire lumen 34, which is parallel to the longitudinal axis 49 of the main lumen 26, so the proximal portion of each pull wire lumen 34 follows the taper of the main lumen 26. In this manner, each pull wire lumen 34 may be a constant distance DLL from the main lumen 26 along the entire length of the sheath 20 (for example, as shown in FIGS. 6 and 7). As a non-limiting example, the proximal portion of each pull wire lumen 34 may be at an angle α of between approximately 5° and approximately 45° (±5°) from the longitudinal axis 48. Accordingly, the taper of the proximal portion of the main lumen 26 may also be at an angle of between approximately 10° and approximately 45° (±5°) from the longitudinal axis 48, with the angle of the taper being substantially the same as the angle at which the proximal portion of the pull wire lumen 34 lies from the longitudinal axis 48.

As shown in FIG. 8 (cross-sectional view of the proximal portion 24 of the sheath 20 taken along line 7/8-7/8 in FIG. 2, shown with the hub 30), when the hub 30 is coupled to the proximal portion 24 of the sheath 20, the proximal opening 46 of each of the one or more pull wires 34 may be left uncovered by the hub 30. In this way, a pull wire 36 may be free to exit the sheath proximal portion 24 without the need for a skive hole. In use, a medical device may be inserted into an opening within the hub 30 (not shown) or an opening of a component coupled to the hub (not shown) and advanced through the introducer sheath 20 and into the patient's vasculature. As shown in FIGS. 6-8, the proximal portion 24 of the sheath 20 may define a proximal face 50 that includes the main lumen proximal opening 40 and the pull wire lumen proximal opening 46. The proximal face 50 may lie in a plane that is at least substantially orthogonal to the longitudinal axis of the sheath 20.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An introducer device, comprising:
   an elongate body having a proximal portion with a proximal opening, a distal portion, and a lumen therebetween, the proximal opening having a first inner diameter and the lumen within the distal portion having a second diameter that is less than the first diameter; and
   a secondary device insertion hub having a tapered shape with a proximal portion having a first outer diameter and a distal portion having a second outer diameter that is less than the first outer diameter,
   at least a portion of the distal portion of the secondary device insertion hub being received within and affixed to the proximal opening of the elongate body.

2. The introducer device of claim 1, wherein the lumen is a main lumen, the introducer device further comprising a pull wire lumen that is substantially parallel to the main lumen, the pull wire lumen including a proximal opening that is unobstructed by the secondary device insertion hub.

3. The introducer device of claim 2, wherein the pull wire lumen has a continuous inner diameter, the pull wire lumen being a distance from the main lumen, the distance being the same in the proximal portion of the elongate body as in the distal portion of the elongate body.

4. The introducer device of claim 2, wherein the proximal portion of the elongate body defines a proximal face, the proximal face surrounding the proximal opening of the main lumen.

5. The introducer device of claim 4, further comprising a pull wire within the pull wire lumen, at least a portion of the pull wire exiting the proximal portion of the elongate body through the proximal face.

6. The introducer device of claim 4, wherein the proximal face defines a proximal opening of the pull wire lumen and the proximal opening of the main lumen.

7. The introducer device of claim 3, wherein the elongate body defines a longitudinal axis.

8. The introducer device of claim 7, wherein a proximal portion of the pull wire lumen is at an angle of between approximately 10° and approximately 45° from the longitudinal axis.

9. The introducer device of claim 8, wherein the main lumen lies along the longitudinal axis.

10. The introducer device of claim 1, wherein the secondary device insertion hub is integrated with the proximal portion of the elongate body.

11. The introducer device of claim 1, wherein the secondary device insertion hub is a hemostasis valve hub.

12. An introducer device comprising:
    an elongate body having a proximal portion, a distal portion, and a longitudinal axis;
    a main lumen defined by the elongate body and extending between the proximal portion of the elongate body and the distal portion of the elongate body, the main lumen having a proximal opening;
    a pull wire lumen defined by the elongate body and extending between the proximal portion of the elongate body and the distal portion of the elongate body, the pull wire lumen having a proximal opening; and
    a secondary device insertion hub,
    the secondary device insertion hub being received within the proximal opening of the main lumen, the proximal opening of the pull wire lumen being unobstructed by the secondary device insertion hub.

13. The introducer device of claim 12, wherein the main lumen has a distal portion having a first inner diameter and a tapered portion between the distal portion and the proximal opening of the main lumen.

14. The introducer device of claim 13, wherein the proximal opening of the main lumen has a second inner diameter and the tapered portion has a continuously decreasing inner diameter from the proximal opening to the distal portion of the main lumen.

15. The introducer device of claim 12, wherein the proximal portion of the elongate body defines a proximal face.

16. The introducer device of claim 15, wherein the proximal face includes the proximal opening of the pull wire lumen and the proximal opening of the main lumen.

17. A medical device comprising:
    an elongate body having a proximal portion, a distal portion, and a longitudinal axis;
    a main lumen defined by the elongate body and extending between the proximal portion of the elongate body and the distal portion of the elongate body along the longitudinal axis of the elongate body, the main lumen having a distal portion, a proximal opening, and a tapered portion between the proximal opening and the distal portion of the main lumen;
    a pull wire lumen defined by the elongate body and extending between the proximal portion of the elongate body and the distal portion of the elongate body, the pull wire lumen having a distal portion, a proximal portion, and a proximal opening; and
    a secondary device insertion hub at least partially disposed within the proximal opening and tapered portion of the main lumen, the proximal opening of the pull wire lumen being unobstructed by the secondary device insertion hub,
    the distal portion of the pull wire lumen being at least substantially parallel to the longitudinal axis and the proximal portion of the pull wire lumen being at an angle from the longitudinal axis that follows an angle of the tapered portion of the main lumen.

18. The medical device of claim 17, wherein the proximal portion of the pull wire lumen is at an angle of between approximately 10° and approximately 45° from the longitudinal axis of the elongate body.

* * * * *